United States Patent [19]

Chien et al.

[11] Patent Number: 4,681,466
[45] Date of Patent: Jul. 21, 1987

[54] METHOD FOR DETERMINING QUALITY OF REDUCED QUALITY STEAM

[75] Inventors: Sze-Foo Chien, Houston; Clifford L. Redus, Katy; Peter L. Sigwardt, Houston, all of Tex.

[73] Assignee: Texaco Inc., White Plains, N.Y.

[21] Appl. No.: 824,812

[22] Filed: Jan. 31, 1986

[51] Int. Cl.[4] .................. G01F 1/34; G01N 25/60
[52] U.S. Cl. ................................. 374/42; 73/195; 73/861.04
[58] Field of Search ............... 374/42; 73/29, 195, 73/196, 861.01, 861.04; 364/509

[56] References Cited

U.S. PATENT DOCUMENTS

| | | | |
|---|---|---|---|
| 3,267,729 | 8/1966 | Cowburn | 73/861.01 |
| 3,898,882 | 8/1975 | Prokopius | 73/195 |
| 3,963,043 | 6/1976 | Cota et al. | 73/195 X |
| 4,028,942 | 6/1977 | Gardiner | 73/29 |
| 4,149,403 | 4/1979 | Muldary et al. | 73/29 |
| 4,542,993 | 9/1985 | Mims | 374/42 |
| 4,561,785 | 12/1985 | Long et al. | 374/42 |
| 4,562,744 | 1/1986 | Hall et al. | 73/861.02 |
| 4,576,036 | 3/1986 | Huang et al. | 73/29 |
| 4,576,043 | 3/1986 | Nguyen | 73/861.04 X |

FOREIGN PATENT DOCUMENTS 0434798 10/1967 Fed. Rep. of Germany ........ 374/42
0917714 2/1963 United Kingdom ................. 374/42

Primary Examiner—Daniel M. Yasich
Attorney, Agent, or Firm—Robert A. Kulason; James J. O'Loughlin; Robert B. Burns

[57] ABSTRACT

In a steam flow line that is delivering reduced quality steam, there is a method and/or system for determining the quality. It includes the steps of flowing quality steam through a first flow restriction, and mixing a measured quantity of water with the steam, downstream from the restriction. It also includes flowing the mixture through a second flow restriction. Then, by measuring pressures and temperatures, the quality of the steam at the second flow restriction may be calculated. Where the pressure drop across the second flow restriction is very small compared to the supply line pressure, the quality of the steam downstream is essentially the same, and thus determined.

5 Claims, 2 Drawing Figures

METHOD FOR DETERMINING QUALITY OF REDUCED QUALITY STEAM

CROSS REFERENCE TO RELATED INVENTION

This application deals with subject matter that is similar to U.S. Pat. No. 4,542,993 issued Sept. 24, 1985, titled Accurate Method of Measuring Steam Quality, which is assigned to the assignee of this application.

BACKGROUND OF THE INVENTION

1. Field of the Invention

This invention concerns a method of measuring quality of steam in a steam flow line. More specifically, it is concerned with a method that is for determining the quality of reduced quality steam, where a determination of the quality is important such as in connection with steam injection in a steam flooding project for oil recovery.

2. Description of Related Art

In addition to the art cited in the above noted related patent, the applicants are aware of two U.S. patents as follows: U.S. Pat. No. 4,028,942, June 14, 1977 to Gardiner titled Hygrometer and U.S. Pat. No. 4,149,403, April 17, 1979 to Muldary et al titled Determining Steam Quality. However, in neither of the foregoing two U.S. patents is there any showing or teaching for the use of a second restriction downstream in accordance with the applicants' invention. Nor, is there any use of the mixing of a known quantity of water between two restrictions. Also, in regard to the foregoing related patent itself, it employs intermittent water injection with a single flow restriction and vertical flow orientation across the restriction. Consequently, it does not show or suggest the applicants' invention.

It is an object of this invention to provide for a method of determining flow line steam quality which uses flow restriction devices with water addition at a known rate between restrictions.

Another object of the invention is to provide for certain field applications where high quality steam is mixed with water to achieve a specific low quality steam. In such case, the quality of the resulting low quality steam may be accurately determined.

SUMMARY OF THE INVENTION

Briefly, the invention is in a steam flow line for supplying reduced quality steam to an injection well or the like. It concerns a method for determining the quality of said reduced quality steam which comprises flowing a supply of relatively higher quality steam through a first flow restriction, and mixing a known quantity of water with said steam downstream from said first restriction. It also comprises flowing said mixture through a second flow restriction, and determining said steam quality using required pressudre and temperature measurements.

Again briefly, the invention is in a steam flow line for supplying a specific reduced quality steam to an injection well or the like. It concerns a system that comprises in combination an insulated steam line, said steam line having a first restriction for reducing the pressure of said steam. It also comprises a second restriction in said steam line downstream from said first restriction, and means for injecting water into said steam line between said first and second restrictions. It also comprises means for measuring the quantity of said water injected, and means for measuring the temperature and pressure of said injected water. It also comprises means for measuring the pressure in said steam line upstream of said first restriction and between said first and second restrictions, all whereby the quality of steam supplied by said steam line may be calculated.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein.

DESCRIPTION OF THE PREFERRED EMBODIMENT

In steam injection for secondary oil recovery procedures, there is a continuing problem with determination of the quality of steam being injected into an individual well. Such knowledge is important because the steam quality directly affects the production operations and consequently the earnings and future investment requirements for steam flooding projects. In some situations high quality steam will be mixed with water to achieve a specific wellhead lower quality steam. And, in such case, this invention provides for the ability to determine the steam quality so that it may be maintained as desired.

Figure 1:
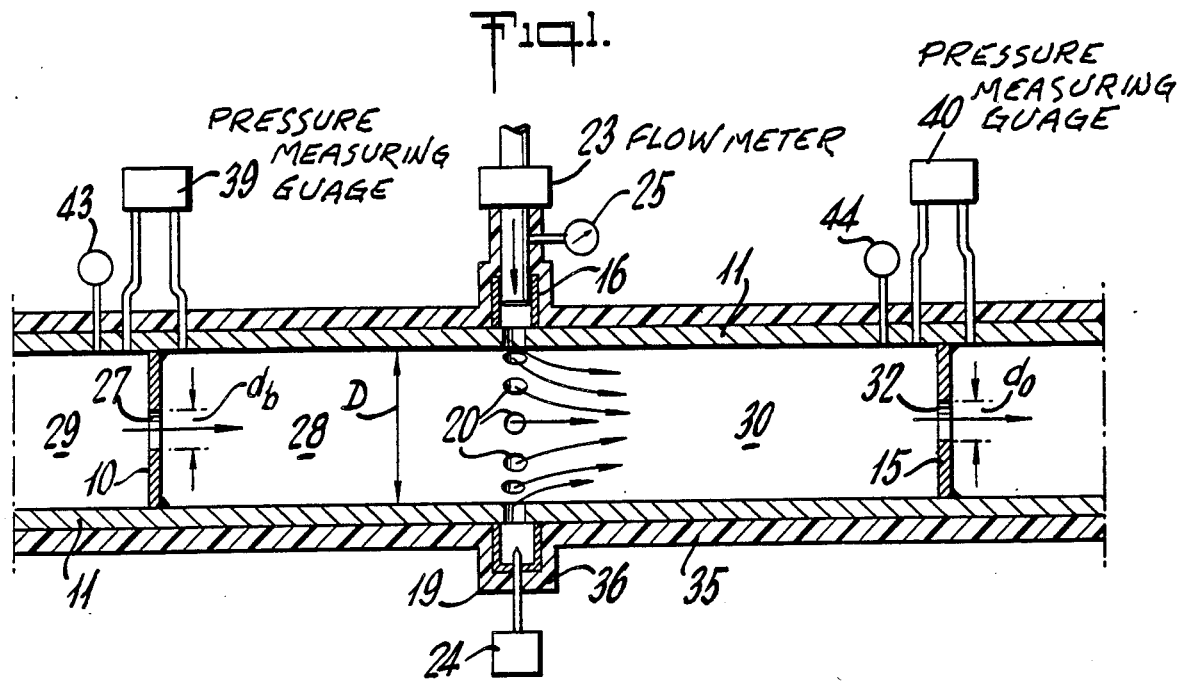
FIG. 1 shows a schematic representation of a steam flow line including a pair of restrictions and an inlet for mixing water, all in accordance with the invention.

FIG. 1 of the drawings illustrates schematically a steam flow line pipe 11 that has high quality steam flowing therein. There is a first restriction 10 in the pipe 11 and a second restriction 15 downstream from the first restriction. Also, there is a spray nozzle 16 located in between the restrictions 10 and 15.

Spray nozzle 16 might take different forms but preferably includes a collar 19 that surrounds the pipe 11, but there is a peripheral series of orifices 20 through which the water that is being mixed into the steam may flow. Thus, mixing water flows to the inside of pipe 11 in between the restrictions 10 and 15.

There is a flow meter 23 for measuring the flow of water delivered to the spray nozzle 16. And, there is a thermocouple 24 for measuring the temperature and a pressure gage 25 for determining the pressure of the water being introduced. It will be understood that any feasible instruments may be employed, e.g. a commercial turbine flowmeter, a commercial pressure gage, and an industrial thermocouple assembly, respectively.

The first restriction 10 may take various forms such as a choke, a pipe, a baffle, a static mixer, an orifice, or a venturi or the like. However, in FIG. 1 it is a schematic illustration that shows an orifice plate with an orifice 27 at the center mounted in the restriction 10 so that the steam must all pass therethrough as it goes from the upstream end in pipe 11 to a downstream location 28 on the inside of the pipe 11. It may be noted that the location 28 has an inside diameter indicated as "D" while the orifice 27 has a smaller inside diameter indicated as "$d_b$." In the description of a preferred embodiment of a method according to this invention, the relationship of the diameters is such as to provide a pressure in location 28 that is smaller than the pressure in an upstream location 29.

The restriction 15 may take the form of any feasible restrictor such as an orifice plate with an orifice 32 at the center that has a diameter which is indicated in the drawing by the caption "$d_o$."

The entire system is well insulated as indicated in the drawing. Thus, there is an insulation coating 35 which covers the pipe 11, and there is an insulation layer 36 that covers the collar 19 and a portion of the nozzle 16 between the meter 23 and the connection with the pipe 11. It will be appreciated that this insulation is sufficient to ensure a negligible amount of heat loss in the system.

At the restrictions 10 and 15 there are differential pressure measuring instruments 39 and 40 respectively. These may take various forms such as commercially available transducers, e.g. a Rosemount differential pressure transducer or its equivalent from another manufacturer. Also, there are static pressure transducers 43 and 44 for measuring the static pressure at locations 29 and 30 respectively. Similarly, these transducers may be those designated as Rosemount static transducers or the equivalent from another manufacturer.

With reference to the system described previously in relation to FIG. 1, a method according to the invention may be carried out as explained by the following, wherein:

$P_1$ is the static pressure at location 29
$P_2$ is the static pressure at location 30
$x_1$ is steam quality just before orifice 29
$x_2$ is steam quality just before orifice 32.

Figure 2:
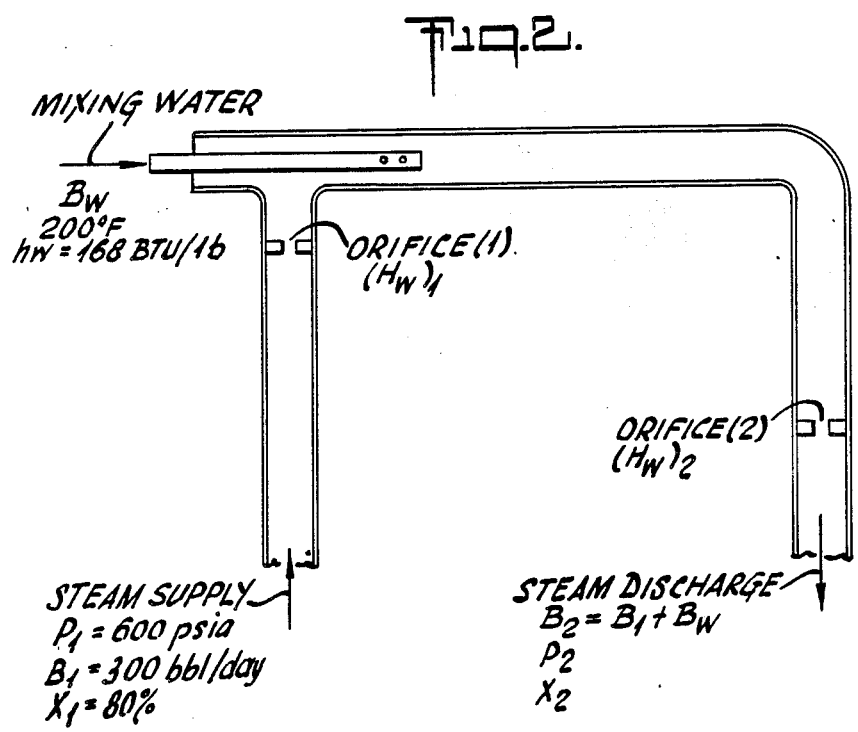
FIG. 2 is a schematic with captions to illustrate the basis for a specific example that is described herein.

In the following derivation, "Point 1" of the FIG. 2 illustration will represent location 29 in FIG. 1 and "Point 2" of the FIG. 2 illustration will represent location 32.

The mixing is achieved by admitting water into the steam flow line (pipe 11) in an annular fashion. The mass flow rate can be calculated for the case of subcritical flow through flow restriction 10 (the pressure at location 28 is greter than half the pressure at location 29) as:

$$\dot{m}_1 = \frac{\beta d_b^2 Y_1}{\sqrt{1 - \left(\frac{d_b}{D}\right)^4}} \sqrt{\frac{H_1}{x_1^{1.5}(v_{fg})_1 + (v_f)_1}} \quad \text{(A-1)}$$

or, $$x_1 = x_1(\dot{m}_1, H_1) \quad \text{(A-2)}$$

(Flow equation from Russell James Paper-Proc. Instn. Mech. Engr. 1961-66, Vol. 180, Pt. 1., No. 23., pg. 562.)
Where, $\dot{m}_1$ is mass flow rate of steam at point 1
$\beta$ is a constant depending on unit of parameters used in the equation
$d_b$ is orifice diameter
D is pipe diameter
$Y_1$ is Expansion Factor which depends on $H_1/P_1$; the James paper has a graph showing Y as a function of $H_1/P_1$
$H_1$ is orifice pressure drop across restriction 10
$x_1$ is steam quality just before entering the orifice 29 at restriction 10
$(v_f)_1$ is specific volume of steam at 0% quality of $P_1$
$(v_{fg})_1$ is change in specific volume of steam from 0% to 100% quality at $P_1$.

For given value of D and $d_b$, measured value of $P_1$ and $H_1$, $x_1$ is a function of $\dot{m}$, only.

It is noted that if the first flow restriction causes critical flow (where $P_2/P_1 < 0.5$), a different form of equation (A-1) is used to calculate the mass flow rate at point 1.

Downstream of the mixing point, the flow rate through the orifice can be written as:

$$\dot{m}_2 = \dot{m}_1 + \dot{m}_i = \frac{\beta d_o^2 Y_2}{\sqrt{1 - \left(\frac{d_o}{D}\right)^4}} \sqrt{\frac{H_2}{x_2^{1.5}(v_{fg})_2 + (v_f)_2}} \quad \text{(A-3)}$$

(Flow equation from Russel James Paper-Proc. Instn. Mech. Engr. 1961-66, Vol. 180, Pt. 1., No. 23., pg. 562.)
Where:

$\dot{m}_2$ is mass flow rate of steam at point 2
$\beta$ is a constant depending on unit of parameters used in the equation
$\dot{m}_i$ is the mass flow rate of water injection
$d_o$ is orifice diameter
D is pipe diameter
$Y_2$ is Expansion Factor which depends on $H_2/P_2$; the James paper has a graph showing Y as a function of $H_2/P_2$
$H_2$ is orifice pressure drop across restriction 15
$x_2$ is steam quality just before entering the orifice 32 at restriction 15
$(v_f)_2$ is specific volume of steam at 0% quality at $P_2$
$(v_{fg})_2$ is change in specific volume of steam from 0% to 100% quality at $P_2$.

This orifice flow equation can be rearranged to give $$x_2 = x_2(\dot{m}_1, \dot{m}_i, d_o, D, H_2, P_2) \quad \text{(A-4)}$$

For a given orifice and pipe, $d_o$ and D are known
$H_2$ is the measured value
$P_2$ is known, and
$(v_f)_2$ and $(v_{fg})_2$ can be taken from the steam tables for known $P_2$ Thus, $$x_2 = x_2(\dot{m}_1, \dot{m}_i) \quad \text{(A-5)}$$

If the water injection rate is prescribed, $x_2$ is only a function of $m_1$:

$$x_2 = x_2(\dot{m}_1) \quad \text{(A-6)}$$

The heat balance of the mixing process is $$\dot{m}_1[(h_f)_1 + x_1(h_{fg})_1] + \dot{m}_i h_i = (\dot{m}_1 + \dot{m}_i)[(h_f)_2 + x_2(h_{fg})_2] \quad \text{(A-7)}$$

Where:
$(h_f)_1$ is the enthalpy of steam at 0% quality at $P_1$ (sensible heat),
$(h_{fg})_1$ is the latent heat of vaporization of steam at $P_1$,
$(h_f)_2$ and $(h_{fg})_2$ are similar quantities at $P_2$, and
$h_i$ is the enthalpy of injected water.

As shown above, $x_1$ and $x_2$ are functions of $\dot{m}_1$ only. The heat balance equation therefore can be written as an equation involving only $\dot{m}_1$:

$$f(\dot{m}_1) = 0 \tag{A-8}$$

By solving equation (A-8), $\dot{m}_1$ is determined. Once $\dot{m}_1$ is determined, $x_1$ and $x_2$ can be calculated from Equations (A-4) and (A-6) respectively.

EXAMPLE

An example of a specific procedure in accordance with the invention is as follows. It illustrates a steam-water mixing/steam quality determination.

Assuming that steam at 600 psia and 80% quality is being supplied at 300 bbl/day through a 2" surface line to a system according to the invention and it is desired to inject steam at 60% wellhead quality, it will be necessary to:
(a) determine the mixing water (at 200° F.) addition rate required to reduce the quality; and
(b) confirm the supply and wellhead steam quality and flow rates by using 1.25 inch orifice plates upstream and downstream of the water addition point.

WATER RATE

Using the heat balance equation and information shown in FIG. 2 of the drawings:

$$B_1 \rho (h_{f1} + x_1 h_{fg1}) + B_w \rho h_w = (B_1 + B_w) \rho (h_{f2} + x_2 h_{fg2}) \tag{B-1}$$

Where:
 $B_1$ = steam supply rate, bbl/day
 $B_w$ = water addition rate, bbl/day
 $\rho$ = density of water, lb/bbl
 $h_f$ = enthalpy of saturated water, Btu/lb
 $h_{fg}$ = enthalpy change from saturated water to saturated vapor, Btu/lb
 $h_w$ = enthalpy of mixing water, Btu/lb.
And:
 $h_1$ = enthalpy of steam before mixing, Btu/lb
 $h_1 = h_{f1} + x_1 h_{fg1}$ (B-2)
 $h_2$ = enthalpy of steam after mixing, Btu/lb
 $h_2 = h_{f2} + x_2 h_{fg2}$ (B-3)

Substituting Equation (B-2) and (B-3) into Equation (B-1) and rearranging gives:

$$B_w = \frac{B_1(h_2 - h_1)}{h_w - h_2} \tag{B-4}$$

At 600 psia:
 $h_{f1} = 471.6$ Btu/lb
 $h_{fg1} = 731.6$ Btu/lb
 $h_1 = 471.6 + 0.80\,(731.6) + 1056.9$ Btu/lb.

Assuming pressure drop across orifices is very small compared to supply pressure of 600 psia:
 $h_2 \approx 471.6 + 0.60\,(731.6) = 910.6$ Btu/lb
 $h_w = 168$ Btu/lb
 $B_1 = 300$ bbl/day.
From Equation (B-4):

$$B_w = \frac{300\,(910.6 - 1056.9)}{(168 - 910.6)} = 59.1 \text{ bbl/day}$$

STEAM QUALITY DETERMINATION

Using James Orifice Flow Equation:*

$$B = \frac{18.778\, Y d_o^2}{\left[1 - \left(\frac{d_o}{D}\right)^4\right]^{0.5}} \frac{H_w^{0.5}}{V_J} \tag{B-5}$$

Where:
 B = steam flow rate, bbl/day
 Y = expansion factor (assumed very close to 1.0 where head loss across orifice is very small compared to supply pressure)
 $d_o$ = orifice diameter, inches
 D = pipe diameter, inches
 $H_w$ = orifice pressure drop, inches of water
 $V_J$ = equivalent specific volume developed by James, ft$^3$/lb
 $V_J = V_f + x^{1.5} V_{fg}$ (B-6)
Where:
 $V_f$ = specific volume of saturated water, ft$^3$/lb
 $V_{fg}$ = change in specific volume from saturated water to saturated vapor, ft$^3$/lb
 x = steam quality.

*Russell James "Metering of Steam Water Two-Phase Flow by Sharp-Edged Orifices," Proc. Instn. Mech. Engrs., Vol. 180, Pt. 1, No. 23, 1965-66, pgs 549–566.

For orifices of 1.25 inches and a 2.00 inch supply line, and assuming $Y \approx 1$ (James paper has a correlation graph showing Y as a function of $H_w/P_2$):
 $V_{J1} = 0.55654$ ft$^3$/lb and $V_{J2} = 0.36838$ ft$^3$/lb
 $B_1 = 42.724(H_w)_1^{0.5}$ (B-7)
 $B_2 = 52.504(H_w)_2^{0.5}$ (B-8)
For $B_1 = 300$ bbl/day
 $(H_w)_1 = 49.3$ inches
For $B_2 = 300 + 59.1 = 359.1$ bbl/day
 $(H_w)_2 = 46.8$ inches.

Using the above orifice head-loss information and the known water addition rate to determine steam quality and flow rate ($x_1$, $x_2$, $B_1$ and $B_2$.) Combining Equations (B-5) and (B-6) and substituting known values for Y, $d_o$, $v_f$, $v_{fg}$ and $d_o/D$:
 Y = 1
 $d_o = 1.25$ inches
 $v_f = 0.0201$
 $v_{fg} = 0.7497$
 $d_o/D = 1.25/2.0$ $$B_1 = \frac{18.778(1.25)^2}{\left[1 - \left(\frac{1.25}{2.00}\right)^4\right]^{0.5}} \left[\frac{(H_w)_1}{0.0201 + 0.7497\, x_1^{1.5}}\right]^{0.5} \tag{B-9}$$

$$B_1 = 31.87 \left[\frac{(H_w)_1}{0.0201 + 0.7497\, x_1^{1.5}}\right]^{0.5}$$

And, $$B_2 = 31.87 \left[\frac{(H_w)_2}{0.0201 + 0.7497\, x_2^{1.5}}\right]^{0.5} \tag{B-10}$$

But, $B_w = B_2 - B_1$ and $(H_w)_1 = 49.3$, $(H_w)_2 = 46.8$ $$B_w = 31.87 \left[ \frac{46.8}{0.0201 + 0.7497\, x_2^{1.5}} \right]^{0.5} -$$

$$31.87 \left[ \frac{49.3}{0.0201 + 0.7497\, x_1^{1.5}} \right]^{0.5}$$

$$\left[ \frac{B_w}{31.87} \right]^2 = \frac{46.8}{0.0201 + 0.7497\, x_2^{1.5}} +$$

$$\frac{49.3}{0.0201 + 0.7497\, x_2^{1.5}} -$$

$$\left[ \frac{(46.8)(49.3)}{(0.0201 + 0.7497\, x_2^{1.5})(0.0201 + 0.7497\, x_1^{1.5})} \right]^{0.5}$$

Substituting $B_w = 59.1$ bbl/day yields:

$$3.439 = \frac{46.8}{0.0201 + 0.7497\, x_2^{1.5}} + \quad \text{(B-11)}$$

$$\frac{49.3}{0.0201 + 0.7497\, x_1^{1.5}} -$$

$$\frac{96.1}{[(0.0201 + 0.7497\, x_2^{1.5})(0.0201 + 0.7497\, x_1^{1.5})]^{0.5}}$$

From the Heat Balance Equation (B-1):
$$B_1(h_{f1} + x_1 h_{fg1}) + B_w h_w = (B_1 + B_w)(h_{f2} + x_2 h_{fg2})$$

And, $h_{f1} \approx h_{f2}$, $h_{fg1} \approx h_{fg2}$
And, $B_1$ from Equation (B-9)

$$B_1 = 31.87 \left[ \frac{(H_w)_1}{0.0201 + 0.7497\, x_1^{1.5}} \right]^{0.5}$$

Solve for $x_2$ as $f(x_1)$ yields $$x_2 = \frac{x_1}{1 + \frac{B_w}{31.87}\left[\frac{0.0201 + 0.7497\, x_1^{1.5}}{(H_w)_1}\right]^{0.5}} - \quad \text{(B-12)}$$

$$\frac{h_{f1} - h_w}{h_{fg}} \left[ \frac{1}{1 + \frac{31.87}{B_w}\left[\frac{(H_w)_1}{0.0201 + 0.7497\, x_1^{1.5}}\right]^{0.5}} \right]$$

Introducing known values:
$B_w = 59.1$ bbl/day
$(H_w)_1 = 49.3$ inches
$h_{f1} \approx h_{f2} \approx h_f = 471.6$ Btu/lb
$h_{fg1} \approx h_{fg2} \approx h_{fg} = 731.6$ Btu/lb
$h_w = 168$ Btu/lb $$x_2 = \frac{x_1}{1 + \frac{59.1}{31.87}\left[\frac{0.0201 + 0.7497\, x_1^{1.5}}{49.3}\right]^{0.5}} - \quad \text{(B-13)}$$

$$\frac{471.6 - 168.0}{731.6} \left[ \frac{1}{1 + \frac{31.87}{59.1}\left[\frac{49.3}{0.0201 + 0.7497\, x_1^{1.5}}\right]^{0.5}} \right]$$

Or, $$x_2 = \frac{x_1}{1 + 0.264\,(0.0201 + 0.7497\, x_1^{1.5})^{0.5}} -$$

$$\frac{0.415}{1 + \left[\frac{3.793}{(0.0201 + 0.7497\, x_1^{1.5})^{0.5}}\right]}$$

Equations (B-11) and (B-13) now contain only $x_1$, and $x_2$ as unknowns. Simultaneous solution of these two equations using an iterative technique such as Newton-Raphson results in:
$x_1 = 80\%$
$x_2 = 60\%$.

Once $x_1$ and $x_2$ are determined, $B_1$ and $B_2$ can be calculated from Equations (B-9) and (B-10).
$B_1 = 300$ bbl/day
$B_2 = 359.1$ bbl/day.

It will be understood in accordance with the foregoing that the applicant's invention provides for the ability to obtain a specific low quality steam. The quality of such steam is accurately found by the procedure. It employs a first flow restriction (such as a choke or the like) and a mixing of a measured quantity of water down stream, followed by flowing the mixture through a second restriction (such as an orifice.) It involves continuous water injection at a steady state of flow. And, by the use of two flow restrictions, it provides the ability to determine the quality of the steam down stream from the orifice.

While the foregoing description and explanation has been provided in considerable detail in accordance with the applicable statutes, this is not to be taken as in any way limiting the invention, but merely as being descriptive thereof.

We claim:

1. In a steam flow line for supplying reduced quality steam to an injection well or the like, a method for determining the quality of said reduced quality steam, comprising;
    flowing a supply of quality steam through an aperture in a first flow restriction, and measuring the pressure drop thereacross,
    reducing the quality of said steam by mixing a known measured quantity of water with the steam through a peripheral plurality of orifices in said flow line, at a predetermined point downstream of said first restriction,
    flowing said reduced quality steam mixture through a second flow restriction, and measuring the pressure drop thereacross, and
    determining the quality of the steam at said second restriction as a function of at least the pressure characteristic of the steam at said first and second restrictions and continuously injecting said quantity of water which is mixed with the steam downstream of the first flow restriction to maintain the reduced quality steam at the second restriction.

2. In a steam flow line method according to claim 1, wherein said first flow restriction reduces the pressure sufficiently to make the flow through the restriction critical.

3. In a steam flow line method according to claim 2, wherein said first flow restriction reduces the pressure to less than half.

4. In a steam flow line method according to claim 1, wherein pressure and temperature measurements in the flow line comprise pressure upstream of said first restriction, pressure down stream of said first restriction and the pressure and temperature of said water.

5. In a steam flow line for supplying reduced quality steam to an injection well or the like, a method for determining the quality of said reduced quality steam, comprising flowing a supply of steam through a first flow restriction, measuring the pressure of said steam upstream of said first restriction, mixing a predetermined quantity of water with said steam through a peripheral plurality of orifices in said flow line downstream of said first flow restriction, flowing said mixture through a second flow restriction, measuring the pressure of said mixture upstream of said second flow restriction, measuring the pressure and temperature of said water, measuring the pressure drop across said second flow restriction, and determining the mass flow rate of said steam upstream of said first flow restriction whereby the qualities of said steam upstream of both said first and said second flow restrictions may be calculated.

* * * * *